United States Patent [19]
Tait et al.

[11] Patent Number: 5,632,986
[45] Date of Patent: May 27, 1997

[54] PHOSPHOLIPID-TARGETED THROMBOLYTIC AGENTS

[75] Inventors: Jonathan F. Tait; Kazuo Fujikawa, both of Seattle, Wash.

[73] Assignee: The University of Washington, Seattle, Wash.

[21] Appl. No.: 441,006

[22] Filed: May 15, 1995

Related U.S. Application Data

[63] Continuation of Ser. No. 934,651, filed as PCT/US92/03960, May 11, 1992 published as WO92/19279, Nov. 12, 1992, abandoned, which is a continuation-in-part of Ser. No. 697,364, May 9, 1991, abandoned.

[51] Int. Cl.$^6$ .......................... A61K 38/17; A61K 38/49; C07K 14/435; C12N 9/72
[52] U.S. Cl. .................... 424/94.64; 424/94.63; 435/212; 435/215; 514/12; 530/350
[58] Field of Search ................ 424/94.63, 94.64; 435/212, 216, 226, 172.3, 215; 514/12; 530/350

[56] References Cited

U.S. PATENT DOCUMENTS

| | | | |
|---|---|---|---|
| 4,536,391 | 8/1985 | Miyazaki et al. | 424/94 |
| 4,564,596 | 1/1986 | Maximenko et al. | 435/177 |
| 4,673,573 | 6/1987 | Ferres et al. | 424/94.63 |
| 4,752,581 | 6/1988 | Robinson et al. | 435/217 |
| 4,937,324 | 6/1990 | Fujikawa et al. | 530/397 |
| 5,011,686 | 4/1991 | Pang | 424/94.1 |
| 5,109,113 | 4/1992 | Caras et al. | 530/350 |

FOREIGN PATENT DOCUMENTS

| | | |
|---|---|---|
| 14027-A | 9/1988 | Australia. |
| 14027-B | 9/1988 | Australia. |
| 0279459 | 8/1988 | European Pat. Off.. |
| 0293567 | 12/1988 | European Pat. Off.. |
| 9109953 | 7/1991 | WIPO. |
| WO9109953 | 7/1991 | WIPO. |
| 9205749 | 4/1992 | WIPO. |

OTHER PUBLICATIONS

Crumpton, M.J., Nature 345:212 (1990) "Protein terminology tangle".
Biological Chemistry Hoppe-Seyler, vol. 371, May 1990 pp. 383–388.
Production and Secretion of Porcine Urokinase in Saccharomyces cerevisiaeIII, , P. G. Zaworski, et al., Gene, vol. 85 (1989), 545.
Purification and Characteristics of Recombinant Single-Chain Urokinase Produced in Escherichia coli, Winkler & Blaber, Biochemistry, 1986, vol. 25, 4041.
Human Placental Anticoagulant Protein: Isolation and Characterization, Funakoshi et al., Biochemistry, 1987, vol. 26, 5572.
Placental Anticoagulant Proteins: Isolation and Comparative Characterization of Four Members of the Lipocortin Family, Tait et al., Biochemistry, 1988, vol. 27, 6268.
Purification and Characterization of Six Annexins from Human Placenta, Romisch & Heimburger, Biol. Chem. Hoppe–Seyler, vol. 371, 383, May 1990.
Interaction of Placental Anticoagulant Protein–I (Lipocortin V) with Model Membranes, Tait et al., Cytokines and Lipocortins in Inflammation and Differentiation, pp. 173–181, 1990 Wiley–Liss, Inc.
Binding of Annexin V/Placental Anticoagulant Protein I to Platelets, Thiagarajan & Tait, Journal of Biological Chemistry, vol. 265, No. 29, 17420, 1990.
Placental Anticoagulant Protein–I: Measurement in Extracellular Fluids and Cells of the Hemostatic System, Flaherty et al., Journal of Laboratory and Clinical Medicine, vol. 115, No. 2, 174, Feb. 1990.
Phospholipid Binding Properties of Human Placental Anticoagulant Protein–I, a Member of the Lipocortin Family, Tait et al., Journal of Biological Chemistry, vol. 264, No. 14, 7944, May 1989.
A Concensus Amino Acid Sequence Repeat in Torpedo and Mammalian $Ca^{2+}$-Dependent Membrane–Binding Proteins, Geisow et al., Nature, vol. 320, 636, Apr. 1986.
Common Domain Structure of $Ca^{2+}$ and Lipid–Binding Proteins, Geisow, FEBS Lett., vol. 203, No. 1, 99, Jul. 1986.
The Crystal and Molecular Structure of Human Annexin V, An Anticoagulant Protein . . . , Huber et al., EMBO Journal, vol. 9, No. 12, 3867, 1990.
The Calcium Binding Sites in Human Annexin V by Crystal Structure Analysis . . . , Huber et al., FEBS Letters, vol. 275, No. 1, 2, 15, Nov. 1990.
Mutant and Chimeric Recombinant Plasminogen Activators, Pierard et al., Journal of Biol. Chem., vol. 262, No. 24, 11771, Aug. 1987.
More Useful Maleimide Compounds for the Conjugation of Fab' to Horseradish Peroxidase . . . , Hashida et al., Journal of Applied Biochemistry 6, 56 (1984).
Plasminogen Activator–Anti–Human Fibrinogen Conjugate, Sevilla et al., Biochemical and Biophysical Research Comunications, vol. 130, No. 1, 91, Jul. 1985.
Primary Structure of Human Placental Anticoagulant Protein, Funakoshi et al., Biochemistry, 1987, vol. 26, 8087.
Principles of Biochemistry, White et al., Sixth Edition, 1978, McGraw–Hill, pp. 916–928.
Construction and Expression of a Recombinant Antibody–Targeted Plasminogen Activator, Schnee et al., Proc. Nat'l. Acad. Sci., vol. 84, 6904, Oct. 1987.
Characterization of a Recombinant Fusion Protein of the Finger . . . , Gheysen et al., J. Biol. Chem., vol. 262, No. 24, 11779 (1987).

*Primary Examiner*—Dian C. Jacobson
*Attorney, Agent, or Firm*—Sughrue, Mion, Zinn, Macpeak & Seas

[57] ABSTRACT

Conjugates with an affinity for phospholipids are disclosed. The conjugates comprise a first compound having affinity for phospholipids, with a binding constant that is not greater than about $10^{-7}M$ and a second compound that lyses thrombi or is a precursor of a compound that lyses thrombi.

3 Claims, 3 Drawing Sheets

PHOSPHOLIPID-TARGETED THROMBOLYTIC AGENTS

Portions of the research described herein were supported in part by grants awarded by the National Institute of Health. The government has certain rights in the invention.

This is a continuation of application Ser. No. 07/934,651 filed as PCT/US92/03960, May 11, 1992 published as WO92/19279, Nov. 12, 1992 which is a continuation-in-part of U.S. application Ser. No. 07/697,364 filed on 9 May 1991 both now abandoned.

FIELD OF THE INVENTION

The invention relates to conjugates and pharmaceutic compositions with affinity for phospholipids and capability of lysing fibrin clots. The invention also relates to methods and therapeutic regimens for treating disorders relating to fibrin clots.

BACKGROUND OF THE INVENTION

Fibrin deposits form at sites of vascular injury including ruptured atherosclerotic plaques. The initial event leading to fibrin formation is the activation of the extrinsic coagulation pathway which is triggered by the contact of tissue factor with circulating factor VII/VIIa. Tissue factor is a membrane-bound regulatory protein present outside blood vessels as well as in atherosclerotic plaques. When tissue factor is exposed to blood by vascular injury or plaque rupture, it binds to factor VII/VIIa in the presence of $Ca^{++}$. The complex of tissue factor and factor VII/VIIa activates factor X to factor Xa, which in turn, activates prothrombin to thrombin in the presence of factor Va, phospholipid and $Ca^{++}$. The resulting thrombin converts soluble fibrinogen to insoluble fibrin which deposits as clots.

The complex of tissue factor and factor VII/VIIa not only activates factor X but also activates factor IX to form factor IXa. Factor IXa activates factor X in the presence of phospholipid, factor VIIIa and $Ca^{++}$. The reactions, except for the conversion of fibrinogen to fibrin, require negatively charged phospholipid, such as phosphatidylserine (PS), for optimal catalysis and proceed at the surface of insoluble phospholipid to localize fibrin clot formation. Thus, major components of fibrin clots are insoluble fibrin, phospholipid and the activated coagulation factors.

Phosphatidylserine, which is highly thrombogenic in vitro, generally is absent from the external face of the plasma membrane in both erythrocytes and platelets. The asymmetry is maintained by an active transport mechanism. It is believed that the asymmetrical distribution of PS is altered by platelet activation and PS becomes exposed on the external face of the plasma membrane. That reorientation provides negatively charged phospholipids for the formation of the prothrombinase complex and also enhances other phospholipid-dependent reactions in the coagulation cascade.

The coagulation factors that contain gamma-carboxyglutamic acid residues (factors X, IX, VII and prothrombin) bind to negatively charged phospholipids with banding constants in the $10^{-6}$–$10^{-7}$M range in the presence of $Ca^{++}$. The major source of negatively charged phospholipids for blood coagulation in vivo is thought to be the platelet plasma membrane. In fact, factor Xa binds to the surface of activated platelets where it forms a complex (prothrombinase) with platelet-bound factor Va to activate prothrombin.

Plasmin, a serine protease, is the sole plasma enzyme responsible for fibrin dissolution. It circulates in blood as a precursor, plasminogen. Plasminogen is a single-chain polypeptide that is converted to the two-chain active form, plasmin, by plasminogen activators. Plasmin is composed of an $NH_2$-terminal A-chain and a COOH-terminal B-chain held together by a disulfide bond. The A-chain contains five characteristic repeating units (kringle domains) while the B-chain contains the serine-protease catalytic unit. The region from the first kringle through fourth kringle binds to fibrinogen and some of the circulating plasminogen coprecipitates with fibrin when a clot is formed. Plasminogen that is proteolytically cleaved (Lys-plasminogen) has a higher affinity for fibrin clots than intact plasminogen (Glu-plasminogen) and thus accelerates lysis of fibrin clots. The fibrin binding sites of plasminogen are located in the first and fourth kringle domains.

Tissue-type plasminogen activator (tPA) and urokinase (uPA) are two physiologic activators of plasminogen. Both activators are synthesized as single-chain zymogens and are converted into two-chain active forms. tPA is a membrane bound protein synthesized mainly in endothelial cells and released into the blood stream in response to certain stimuli. The secretion of tPA into the blood stream triggers extrinsic fibrinolysis. The $NH_2$-terminal chain of tPA contains a finger domain, a growth factor-like domain and two kringle domains. The second kringle domain has binding affinity ($K_d$, also known as binding constant or affinity constant) for the fibrin clot of $1.6 \times 10^{-7}$M. The catalytic efficiency of tPA is about 1,000 times higher toward fibrin-bound plasminogen than circulating plasminogen.

Prourokinase (single-chain urokinase or scuPA), a precursor of urokinase, is present in blood at low concentrations. Prourokinase is activated by plasma kallikrein and plasmin to stimulate intrinsic fibrinolysis. Although scuPA has a kringle domain, it shows little binding affinity for fibrin clots. However, it hydrolyzes fibrin-bound plasminogen more efficiently than free plasminogen.

A bacterial protein, streptokinase (SK), forms a stoichiometric complex with plasminogen which converts plasminogen to plasmin.

Fibrinolytic agents, tPA, uPA, scuPA and SK are being used as therapeutic agents to treat patients suffering from thrombosis. Although the agents represent a major advance, problems remain due to short half-life in circulation and a propensity to cause systemic fibrinogenolysis. For example, the relatively insufficient binding affinity for fibrin and probable cross-binding to circulating fibrinogen force a high-dose administration of tPA, which causes a significant degree of fibrinogenolysis.

The above therapeutic proteins have been modified in attempts to overcome the above-noted problems. The strategies used for improvements include: making the molecules resistant to circulating inhibitors; strengthening binding affinity for fibrin clots; and targeting fibrin deposits by conjugating plasminogen activator with antibody specific to fibrin clots.

Acylated plasminogen/SK (APS) has a higher fibrin selectivity than SK. The APS conjugate is not inactivated by a $\alpha_2$-plasmin inhibitor because the hydroxygroup of the active site serine residue is blocked. APS binds to fibrin clots and its acyl group is cleaved slowly to produce the active form. The half-life of APS is significantly longer than that of the unmodified parent molecule.

A truncated scuPA (residues 1–143 deleted) which lacks the growth factor and kringle domains in the heavy chain was expressed. The molecule has a fibrin selectivity identical to the intact form but is not inhibited by plasminogen activator inhibitor-1 (PAI-1).

A modified tPA where the binding site (residues 296–302) to PAI-1 was deleted by site-directed mutagenesis was also expressed. The molecule has the same enzyme activity as the native tPA but had a strong resistance to inhibition by PAI-1 and other setpins in circulating blood.

A chimeric molecule that combined the fibrin binding domain of plasminogen (A-chain) with the catalytic domain of urokinase had a eight-fold higher binding affinity for fibrin clots than urokinase. It also had a higher catalytic activity toward the fibrin monomer.

A chimeric molecule composed of the A chain of plasminogen and the catalytic domain of tPA had the same binding affinity for fibrin as plasminogen and the same catalytic activity as native tPA.

Murine monoclonal antibodies specific to the beta-chain of fibrin were conjugated with the catalytic chain of tPA or scuPA using a disulfide cross-linking agent. The antibodies have dissociation constants on the order of $2 \times 10^{-7}$M. The antibody/tPA conjugate was ten times more active than native tPA in lysis of the fibrin monomer. An antibody/urokinase conjugate showed 1,000 times higher activity than urokinase.

Several proteins with anticoagulatory activity have been isolated from human placenta. proteins were found to be members of the lipocortin/annexin family end to date, eight members of the family have been isolated from various tissues and cultured cells with many different functions proposed. The proteins are given the common name, "annexin". All annexins share the property of calcium-dependent binding to anionic phospholipids. Funakoshi et al., Biochem. (1987a) 26, 5572–5578; Tait et al., Biochem. (1988) 27, 6268–6276; Römisch and Helmburger, Biol. Chem. Hoppe-Seyler (1990) 371, 383–388.

Annexin V (also known as PAP-I) is a major component of the family and is isolated from placenta. It contains one free sulfhydryl group and does not have any attached carbohydrate chains. The primary structure of annexin V deduced from the cDNA sequence shows that annexin V comprises four internal repeating units (each unit has 60–80 amino acid residues). EPA 0 279 459; U.S. Pat. No. 4,937,324; Funakoshi etal., Biochem. (1987b) 26, 8087–8092. Among annexins, annexin V has the strongest binding affinity ($K_d < 10^{-10}$M) for phospholipid vesicles containing 80% phosphatidylcholine (PC) and 20% PS under conditions that are comparable to plasma and extracellular fluid (1.2 mM ionized calcium, 0.15M ionic strength). Annexin shows high affinity for membranes containing PS and phosphatidic acid (PA), phospholipids carrying two negative charges. Tait & Gibson (1990) Cytekines Lipocortin Inflam. Diff., pp. 173–181. Binding is reversible and completely calcium-dependent.

Annexin V binds to human platelets. Unstimulated platelets express a small number of binding sites, but the number of binding sites is increased greatly by certain platelet agonists (for example, approximately 15–20 fold by a combination of thrombin and collagen). There are approximately 100,000 binding sites per platelet after stimulation with thrombin and collagen. The binding sites have an apparent dissociation constant ($K_d$) of 7 nM. The binding is calcium-dependent, reversible and can be inhibited completely by PS-containing vesicles. Annexin V also can displace previously bound factor Xa from the platelet surface. Thiagarajan & Tait, J. Biol. Chem. (1990) 265, 17420–17423.

Annexin V inhibits all of the activation reactions in the coagulation cascade where phospholipid is involved. To catalyze the reactions, gamma-carboxyglutamic acid-containing coagulation factors bind to negatively charged phospholipids in the presence of $Ca^{++}$. The dissociation constants of the γ-carboxyglutamic acid-containing coagulation factors for phospholipid are in the $10^{-6}$–$10^{-7}$M range, which is three to four orders of magnitude weaker than that of annexin V. (For the purposes of the instant invention, greater dissociation constants are those with greater numerical molarity values, thus a constant of $10^{-8}$M is greater than a dissociation constant of $10^{-10}$M. But of course, fort he present invention, a dissociation constant of $10^{-10}$M represents greater binding propensity than a constant of $10^{-8}$M). The inhibition mechanism of annexin V is to compete with the coagulation factors for binding to anionic phospholipids.

Levels of annexin V in human plasma and cells in contact with blood were measured by ELISA using an affinity purified rabbit antiserum. Annexin V is present intracellularly in platelets, endothelial cells and leukocytes but is absent in erythrocytes. Annexin V essentially is not present in normal human plasma and can be released by cell damage or death. Thus the protein that appears to be intracellular under most normal conditions can be released into the extracellular milieu with cell damage or death. Flaherty et al., J. Lab. Clin. Med. (1990) 115, 174–181.

In order to further improve fibrinolytic agents, a higher binding affinity for thrombi is desirable. The affinity of annexin V for negatively charged phospholipids is approximately 50 times stronger than that of tPA for fibrin and 10–100 times stronger than that of fibrin-specific antibodies.

SUMMARY OF THE INVENTION

An object of the invention is to provide annexin-plasminogen activator conjugates useful for thrombolysis.

Another object of the instant invention is to provide methods for making annexin-plasminogen activator conjugates.

Another object of the instant invention is to provide therapeutic compositions and therapeutic methods comprising annexin-plasminogen activator conjugates for treating disorders resulting from thrombosis.

DETAILED DESCRIPTION OF THE INVENTION

Figure 1:
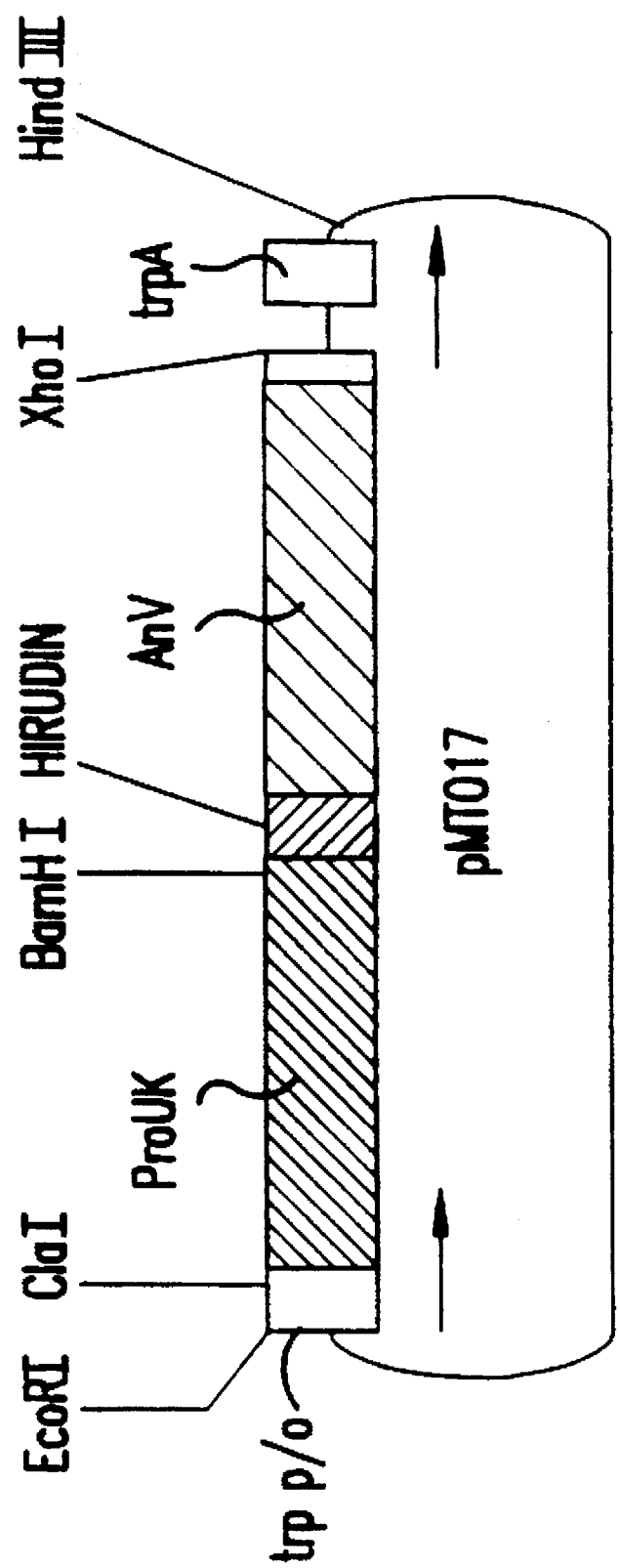
FIG. 1 depicts a map of recombinant plasmid pMT017. The trp promoter region is denoted as trp p/o, the prourokinase coding region as ProUK, the hirudin linker as HIRUDIN, the annexin V coding region as AnV and the trp attenuator as trpA. Commonly known and useful restriction sites are denoted.

The annexins may be isolated from a variety of tissue extracts. Funakoshi etal. (1987a) supra; (1987b) supra; Tait etal. (1988) supra; U.S. Pat. No. 4,937,324. Suitable tissues include liver, lung and placenta. A particularly suitable tissue is human placenta. Briefly, the tissue is cut into small pieces and washed with chilled physiologic buffer, such as phosphate buffered saline or 50 mM Tris-HCl, pH 7.9 containing 50mM NaCl. The tissue chunks are homogenized in a blender generally in a physiologic buffer containing 5 mM EDTA and 5 mM benzamidine. The homogenate is filtered to obtain a filtrate.

The filtrate is next exposed to a precipitation procedure, for example ammonium sulfate. Ammonium sulfate is added to the filtrate to a saturation from about 30% to about 50%. Precipitates formed therefrom are removed by centrifugation. Additional ammonium sulfate is then added to the supernatant to a concentration for about 70% to about 90% and any precipitates formed therefrom are collected by centrifugation. The precipitates are pooled and dissolved in a physiologic buffer, such as those noted above, and the resulting solution is dialyzed overnight against large volumes of physiologic buffer to remove the ammonium sulfate. The buffer is changed at regular intervals.

The dialysate then is passed over an anion exchange medium such as DEAE coupled to, for example, Sephadex, cellulose and Sepharose. Adsorbed proteins are eluted with a linear gradient of increasing salt concentration, for example from about 50 mM to about 500 mM NaCl. Annexin-containing fractions (assay described below) are pooled.

Pooled fractions are concentrated for example, by repeat ammonium sulfate precipitation, polyethylene glycol precipitation or ultrafiltration. If necessary the samples are dialyzed against the physiologic buffer. The samples are then passed over a gel filtration column. A suitable gel filtration column comprises a matrix of Sephadex G-75. Active fractions were collected, pooled and dialyzed to reduce the salt concentration.

The dialysate then is exposed to a cation exchange medium. Suitable cation exchange media include CM-Sephadex, SP-Sephadex, CM-cellulose or Mono S (Pharmacia). The adsorbed proteins are eluted with a buffer gradient of increasing salt concentration. Active fractions are pooled and concentrated as described above.

If placenta is used as a tissue source, several different species of annexin can be obtained. In the above described purification scheme, the species are distinguishable following the ion exchange chromatography and thus the species are distinguishable by solution at differing salt concentration.

Degree of purification can be determined by, for example, SDS-PAGE under reducing or non-reducing conditions using procedures that are recognized in the art. The annexins obtained from placenta so far identified have molecular weights in the range of 30,000 to 35,000. Accordingly, gels of appropriate polyacrylamide concentration are selected.

Several different characteristics of annexins can be monitored. For example, annexin shows an anti-coagulant activity. One such anti-coagulant assay method incorporates rabbit brain cephalin. One vial of cephalin (Sigma) is suspended uniformly in 100 ml of saline. Equal volumes of cephalin and 0.033M $CaCl_2$ are mixed. In another tube acid washed kaolin is suspended in saline at a concentration of 5 mg/ml.

Then 20 µl of pooled normal human plasma, 20 µl of the kaolin suspension and 10 µl of test sample were mixed and incubated for 10 minutes at 37° C. Finally, 40 µl of the cephalin-calcium mixture is added and clotting time is determined.

Assays that measure inhibition of the intrinsic coagulation (kaolin-induced coagulation) pathway can be modified readily to measure inhibition of the extrinsic coagulation pathway (Kondo et al., Thromb. Res. (1987) 48, 449–459. Clotting time is determined, for example by the method described above except that the kaolin suspension is replaced by thromboplastin. Human brain thromboplastin is diluted with 50 mM Tris-HCl, pH 7.4, containing 0.15M NaCl to obtain a controlled clotting time of approximately 60 seconds.

Annexins also show an affinity for phospholipids. One method for quantifying the degree of annexin binding to phospholipids is founded on fluorescence quenching. (Tait et al., J. Biol. Chem. (1989) 264, 7944–7949) Annexin (50 µM) is labeled by incubating with fluorescein isothiocyanate (50 µM) for one hour at 37° C. in a buffer of 0.05M borate, pH 9.0, 0.15M NaCl, 1 mM EDTA. The reaction mixture is dialyzed against 20 mM HEPES pH 8.0 buffer. The dialysate is applied to a cation exchange column and eluted with a linear salt gradient. Annexin labeled with one fluorescein molecule eluted at 0.27M NaCl and multiple fluoresceinated forms of annexin sluts at salt concentration between 0.30M and 0.45M NaCl.

Next, phospholipid vesicles are prepared by adding approximately, 20% PS, 20% diheptanoyl-phosphatidylcholine and 60% long chain PC resulting in the spontaneous formation of unilamellar vesicles. Aliquots of phospholipid stock solutions in chloroform are mixed to yield the desired molar ratios and the chloroform is removed by evaporation under nitrogen. The phospholipids are then dissolved in HEPES buffer by sonication for 3 minutes on ice followed by overnight equilibration at 4° C.

Fluorescence measurements can be performed in a fluorometer (for example, SLM 8000 C/Aminco, Urbana, Ill.). The appropriate wavelengths are selected, for example, for fluorescein the excitation wavelength is 495±16 nM and emissions are monitored at 520±10 nM.

Binding assays are performed in standard quartz fluorescence cells containing a buffer and the fluorescence labeled annexin. The solution is mixed once by inversion and then varying amounts of phospholipids are added to the cuvette. The contents are mixed again by inversion and fluorescence intensity is recorded. Following addition of 5 mM EDTA to the cuvette, fluorescence intensity is recorded again. The degree of quenching is calculated from the ratio of the final fluorescence intensity to fluorescence intensity in the presence of EDTA.

Binding of annexin to phospholipid vesicles occurs with high affinity ($K_d < 10^{-10}M$) under conditions that are comparable to that of plasma and extracellular fluid (1.2 mM ionized calcium, 0.15M ionic strength). Binding is reversible and completely calcium dependent.

Other assays that are suitable for monitoring the presence of annexin include for example antibody-based methods such as ELISA and Western blot.

Alternatively, annexin can be produced by recombinant methods. cDNA clones can be obtained using antibody screening of expression libraries or using oligonucleotide probes deduced from annexin peptides. A full length cDNA clone of annexin V has been obtained and subcloned in expression vectors. Funakoshi et al. (Biochem. (1987a) 26, 5572–5578; (1987b) 8087–8092) used an affinity-purified antibody to screen a cDNA bank to obtain an annexin V clone. A 1.3 kb NcoI/HindIII fragment containing the coding sequence of annexin V was cloned into the expression vector pKK233.2 (Pharmacia) to form the expression plasmid pPAP-I-wt. The recombinant annexin is expressed cytoplasmically at a level of about 2% of cellular protein. The recombinant annexin is obtained from host cells using procedures recognized in the art.

Annexin V contains four tandem, imperfect repeats of about 75 amino acid residues (Funakoshi et al. Biochem. (1987b) 26, 8087–8092). The repeats contain conserved amino acid residues at 4 sites, 15 positions comprise hydrophobic amino acid residues, 4 positions comprise hydroxyamino acids and 2 sites comprise acidic amino acids.

Each of the four repeating sequences contains two regions that are commonly present in phospholipid binding proteins. The first region, the $NH_2$-terminal 17 residues, conforms to a consensus sequence (Gelsow etal., Nature (1986) 320, 636–638) of Lys-Gly-X-Gly-Thr-Asp-Glu-X-X-h-X-h-h-X-Ser-Arg (SEQ ID NO: 1), where h represents hydrophobic amino acids and X can be any amino acid. The sequence has been found in $Ca^{++}$ regulated membrane binding proteins such as endonexin and calelectrin. Phospholipase $A_2$ and a viper venom phospholipase $A_2$ inhibitor also have closely related sequences. The second homologous region in the proteins is a stretch of six residues of hydrophobic amino acids at the C-terminal portion of each repeat. The two regions are thought to be involved directly in binding to phospholipid (Gelsow, FEBS Lett. (1986) 203, 99–103). The strong anticoagulant activity can be attributed to the presence of the phospholipid binding regions. The crystallographic analysis of annexin V showed that the four domains of annexin V have a similar folded structure, each consisting of five a helices (Huber etal., EMBO J. (1990) 9, 3867–3874). The same group also found three strong calcium binding sites of annexin V located on the convex face of the I, II and IV repeats. Huber etal. suggest the calcium binding sites mediate the phospholipid binding to the annexin V molecules (Huber etal. FEBS Lett. (1990) 275, 15–21).

The annexin molecule can be subdivided or altered at one or more amino acid residues so long as the phospholipid binding capability is not reduced substantially. Thus annexin can be truncated, for example, to include one or more domains or contain fewer amino acid residues than the native protein, or can contain substituted amino acids. Any changes are acceptable within the scope of the invention so long as the mutein or second generation annexin molecule does not contain substantially lower affinity for phospholipid. Substantially lower affinity is a binding constant for phospholipid that is greater than about $10^{-7}M$.

Similarly, the fibrinolytic agent can be modified or altered within the scope of the invention so long as the resulting agent retains the capability of lysing fibrin clots. For example, point mutated, point deleted, point substituted and/or truncated fibrinolytic agents, such as tPA, urokinase or prourokinase in which one or more domain(s) has (have) been deleted, can be employed herein. See Wikstrom etal., Fibrinolysis (1990) 5, 31–41 and Van Zonneveld et al., Proc. Natl. Acad. Sci. USA (1986) 83, 4670–4674 on deletion tPA molecules. Other tPA deletion products as well as urokinase and prourokinase deletion molecules are contemplated for use herein. EP 266032A, EP 299706A, EP 308716A, EP 236040A, EP 247674A, EP 253241A, US 4,753,879, WO 87/04722 and JPA 63/230084, among others, describe various altered or modified prourokinase, urokinase and tPA molecules. U.S. Pat. No. 4,752,581, U.S. Pat. No. 4,908,204, U.S. Pat. No. 4,992,274, U.S. Pat. No. 4,916,071 and EP 2311883A describe hybrid molecules such as urokinase/tPA molecules.

The proteolytic properties of modified fibrinolytic agents can be assessed in known assays such as using the chromogenic substrates, S-2288, S-2444 or S-2251 (Helena Laboratories) as taught in Schnee et al. (Proc. Natl. Acad. Sci. (1987) 84, 6904–6908) or as taught in Bode et al. (J. Biol. Chem. (1987) 262, 10819–10823). A reduction of fibrinolysis activity of up to about 50% in a modified fibrinolytic agent relative to the native protein is contemplated to fall within the scope of the instant invention.

Among the many properties of annexin and particularly annexin V that is beneficial to the instant invention is affinity for thrombus or thrombi. Annexin V can target a thrombus in vivo. Radiolabeled annexin V wag administered intravenously and the localization of radio activity was determined. A substantial accumulation was noted at the thrombus with a thrombus:blood ratio of about 17:1 at 100 minutes after injection. The radiolabeled annexin V was rapidly cleared from the blood.

Thus annexin can be used to target a thrombus wherein it may exert its anticoagulant activities or annexin can serve as a means for targeting a second molecule conjugated thereto. Suitable second molecules include thrombolytic agents such as tissue plasminogen activator, streptokinase, urokinase and prourokinase. Annexin conjugates are particularly useful for thrombolytic agents that are not fibrinophilic such as urokinase. Many thrombolytic agents, such as streptokinase, urokinase, prourokinase and tissue plasminogen activator, are available commercially, either produced recombinantly or purified from natural sources. (For example, see U.S. Pat. Nos. 4,853,330; 4,766,075 for tPA; Williams, Brit. J. Exp. Path. (1951) 32, 530 and U.S. Pat. Nos. 2,989,440, 2,983, 647 and 3,081,236 for urokinase; Christensen, Gen. Physiol. (1954) 28, 363 and U.S. Pat. Nos. 3,138,542, 3,226,304, 3,016,337 and 3,107,203 for etreptokinasel and for prourokinase see EPA 0 139 447.)

Through selective proteolytic digestion or subcloning, second generation forms of thrombolytic agents have been produced with the advantages of having enhanced fibrin binding and enhanced half-life, for example, while minimizing adverse side effects. Thus, tPA lacking the epidermal growth factor and finger domains or containing Just the second kringle and serine protease domains have been made. Also, chimeric thrombolytic agents, for example comprising portions of urokinase and tPA, are active in activating plasminogen (Pierard et al., J. Biol. Chem. (1987) 262, 11771).

Annexins can be cross-linked chemically with thrombolytic agents. For example, U.S. Pat. No. 4,564,596 teaches the use of an aliphatic diamine to conjugate urokinase with fibrinogen. U.S. Pat. No. 4,536,391 teaches a plasmin urokinase complex using a coupling reagent of the succinimide ester variety. Sevilla et al. (Biochem. Biophys. Res. Comm. (1985) 130, 91–96) teaches the conjugation of urokinase and an anti-human fibrinogen antibody, bridging the two elements with the heterobifunctional coupling reagent, N-succinimidyl 3-(2-pyridyldithio) propionate (SPDP). There urokinase was reacted with SPDP and separately the antibody was mixed with 2-iminothiolane. The SPDP-modified urokinase was then mixed with the iminothiolated antibody to produce the conjugates. The conjugates were purified by affinity chromatography.

Hashida et al. (J. Appl. Biochem. (1984) 6, 56–63) teach a number of maleimide compounds useful for conjugating proteins. Briefly scuPA, SK or plasminogen is incubated with sulfosuccinimidyl 4-(N-maleimidomethyl) cyclohexane-1-carboxylate (SMCC) in a phosphate buffer, pH 7.0. SMCC binds covalently to free amino groups preferably to the $NH_2$-terminal amino group under these conditions. The reaction mixture then is applied to a gel filtration column to remove side products.

The number of SMCC molecules that are bound to the protein of interest is assessed using 4,4'-dithiodipyridine. When 1.5 molar excess of SMCC is used, the incorporation of 1.2–1.5 moles of SMCC into protein is expected according to established methods. Next, SMCC-protein, for example SMCC-scuPA, SMCC-SK or SMCC-plasminogen, is incubated with annexin V in a phosphate buffer, pH 6.0, containing 6M urea or 6M guanidine. The SMCC-proteins bind specifically to the single free sulfhydryl group present at the C-terminal end (fifth residue from the C-terminus) of the annexin V molecule. The reaction product is applied to a gel filtration column (for example, Sephadex G-100) to isolate the monomeric form, which is expected to be the major product under those conditions. (The annexin V/plasminogen hybrid is activated to form annexin V/plasmin by urokinase. Annexin V is resistant to mild digestion by most proteases under native conditions.)

The compounds for conjugating annexin and thrombolytic agent can be varied to provide a spacer should steric effects compromise either annexin binding affinity or thrombolytic agent activity or both. For example Hashida et al. (supra) teaches compounds with variable numbers of methylene group between the maleimide and succinimide functions and the diamine bridging agent of Maximenko et al. (supra) comprises an aliphatic diamine with 1–12 methylene groups.

Similarly, spacer regions can be configured into recombinant conjugates by inserting appropriate coding sequences between the annexin and thrombolytic agent coding sequences.

Conjugates can also be prepared recombinantly as many of the above recited thrombolytic agents have been cloned. For example, Schnee et al. (Proc. Natl. Acad. Sci. (1987) 84, 6904–6908) teach the expression of a fibrin monoclonal antibody-tPA conjugate by recombinant means. Thus, the heavy chain gene of the anti-fibrin antibody was inserted adjacent to the tPA β-chain gene in an expression vector and recombinant hybrid protein was produced. Pierard et al. (J. Biol. Chem. (1987) 262, 11771–11778) constructed a series of recombinant plasminogen activators comprising domains obtained from urokinase or tPA. The corresponding nucleic acid sequences to the different domains were excised and recombined to produce chimetic coding sequences that in turn produced chimetic protein.

The artisan determines the host in which to express recombinant conjugates. For example, E. coli, B. subtillis, yeast and mammalian cells can be used. The cassette containing the coding sequence is placed into the operable site of an appropriate expression vector comprising the necessary host cell recognizable 5' non-coding sequences including promoters and downstream 3' non-coding sequences. A suitable E. coli expression vector is pKK233-2 (Amann & Brosius, Gene (1985) 40, 183–190); a suitable yeast expression vector is DPOT (Thim et al., Proc. Natl. Acad. Sci. 83, 6766–6770); and a suitable mammalian cell expression vector is pDSP1.1BGH (Pfarr et al., DNA (1985) 4, 461–467).

The domains discussed above may contribute jointly or severally to phospholipid binding and the anticoagulant activity. Accordingly, nucleotide coding sequences of one or more domains or duplicates of one domain can be subcloned adjacent to the coding sequence of the thrombolytic agent to produce conjugates with novel or enhanced properties.

The conjugates can comprise the active component of pharmaceutic compositions. Such compositions would contain pharmaceutically acceptable carriers, diluents and excipients. For example, suitable carriers include buffers, physiologic saline, tissue culture medium and water. The conjugates can be administered using art recognized methods such as in, ravenous infusion. The treatment regimen is determined empirically from animal studies and clinical trials, and is keyed to the severity of the disease, physical condition of the patient and the like. The artisan can obtain suitable guidance from many of the treatises in pharmacology such as, "Goodman & Gilman's The pharmaceutical Bases of Therapeutics" (6th Ed., Goodman et al., ads., MacMillan Publishing Co., New York 1980).

In another embodiment, the targeting capability of annexin can be used to deliver pharmaceutics to local sites. Thus the artisan can use the methods described herein to conjugate a pharmaceutic to annexin. For example, a cytotoxic agent, mitogen, antibiotic and the like can be used. As with other pharmaceutics, delivery route and dosage can be ascertained by the artisan practicing methods known in the art.

The invention will be exemplified further in the following non-limiting examples. Amounts are stated in terms of w/w or w/v.

EXAMPLE I

Iodinated annexin V is prepared using standard procedures such as methods using the Iodogen reagent. Thiagarajan and Tait, J. Biol. Chem. (1990) 265, 17420–17423. The animal model of arterial thrombosis is essentially that described earlier for dogs but adapted to rabbits (Ritchie et al., Circulation (1986) 73, 1006–1012) as described above. A rabbit is intubated, anesthetized with 1–2% halothane and monitored continuously by electrocardiogram. The artery of interest (carotid or femoral) is exposed and a 2–5 cm section is isolated between two ligatures. The section is crushed repeatedly with forceps, the proximal ligature is released for 1 minute to allow fresh blood to enter and then retightened. After two hours, radiolabeled $I^{125}$-annexin V is injected as a bolus via a peripheral vein and the ligatures released thirty seconds later. After a variable period to allow accumulation of the annexin V at the clot and clearance of unbound annexin V from the blood pool, the artery is removed, fixed in formalin, sectioned and measured for radioactivity.

EXAMPLE II

PCR (U.S. Pat. Nos. 4,683,195; 4,683,202) is used to amplify an annexin V cDNA with a 5' NcoI terminus and a 3' XbaI terminus obtained from the plasmid pPAP-I-1.6. Likewise, a scuPA cDNA is amplified by PCR with a 5' XbaI site and a 3' HindIII site. Primers for scuPA are designed from the published cDNA (Holmes et al., Bio/Tech (1985) 3, 923–929) and amplification can be from a cDNA library. The two PCR products are digested with NcoI and XbaI; and XbaI and HindIII, respectively, and are then ligated into an E. coli expression vector such as pKK233-2 (Amann & Brosius, Gene (1985) 40, 183–190) previously digested with NcoI and HindIII. The plasmid is placed into an appropriate host such as DH5α. Recombinants are identified by colony hybridization, and the construction verified by restriction mapping and DNA sequencing. The expression level of the hybrid protein in E. coli is then optimized by varying incubation temperature and the length of the induction period with IPTG.

It is likely the hybrid protein will be packaged in inclusion bodies as occurs with annexin V and scuPA individually (Winklet & Blaber, Biochem. (1986) 25, 4041–4045). The inclusion bodies are isolated by centrifugation (10 minutes at 10,000×g), solubilized in 6M urea and renatured by dialysis. The hybrid protein then is purified by conventional low-pressure and FPLC chromatographic methods, with fractions monitored by fluorescence polarization immunoassay using anti-annexin antibody. The hybrid protein can be characterized in the same manner as described for chemically produced hybrids.

An alternative approach of expression is through a secretory pathway in yeast with, for example, the vector DPOT (Thim et al., Proc. Natl. Acad. Sci. (1986) 83, 6766–6770). Both annexin V and scuPA (Zaworski et al., Gene (1989) 85, 545–551) have been expressed successfully in *Saccharomyces cerevisiae*.

EXAMPLE III

Cultures of E. coli containing the desired plasmid are grown overnight at 37° C. in L broth containing 100 µg/ml ampicillin. Cultures are diluted 1:10 in 1 liter of the same medium and grown at 37° C. with shaking until the $A_{600}$ is>0.3. Synthesis then is induced by adding IPTG to 3 mM and growth continued for 4 hours. Bacteria are harvested by centrifugation, washed once with 100 ml PBS containing 10 mM EDTA and stored at −20° C. Pellets are lysed by sonication for 2–3 minutes on ice in 25 ml of a buffer consisting of PBS, 10 mMEDTA, 6M urea, 0.5 µg/ml leupeptin, 0.5 µg/ml pepstatin, 1% Triton X-100 and 0.2 mM phenylmethanesulfonyl fluoride. The extract is centrifuged (20 minutes at 25000×g). The supernatant is dialyzed at 4° C. against a buffer comprising 50 mM Tris-HCl, pH 8.0, 0.5 µg/ml leupeptin, 0.5 µg/ml pepstatin, 1 mMEDTA, 3mM $NaN_3$ and 100 mM NaCl, with repeated buffer changes. The dialysate is membrane filtered and is applied to an affinity column, for example, an anti-annexin column, at 4° C. The column is washed with at least 100 ml of the same buffer used for dialysis and bound proteins are eluted with 0.1M glycine, pH 2.5 buffer. The eluate is collected in one-fourth volume of 1M Tris-HCl, pH 8.0 for immediate neutralization of pH and then subjected to dialysis and concentration.

EXAMPLE IV

Human annexin binds to rabbit platelets in a manner similar to when annexin binds to human platelets, indicating that the rabbit can be used as an experimental model to test the activity of annexin V hybrids.

Thrombi were induced experimentally by mechanical trauma and stasis in the carotid artery of a rabbit. Radiolabeled annexin V ($^{125}$I-annexin V, 150 uCi) was given as a single intravenous injection 2 hours later. Serial blood samples were then taken at 5, 10, 15, 30 and 60 minutes to determine blood clearance rate; the animal then was sacrificed at 100 minutes and samples of blood, urine and tissue were taken for measurement of weight and $^{125}$I content. No signs of acute systemic toxicity were noted.

As can be seen in Table I, the $^{125}$I-annexin V accumulated substantially at the thrombus, with a thrombus:blood ratio of 17:1 at 100 minutes after injection. Accumulation in intact blood vessels (aorta and vena cava) and most other tissues was minimal. The $^{125}$I-annexin V was cleared rapidly from the blood with a half-life of 10 minutes.

Clearance was primarily through the kidney as indicated by the accumulation of radioactivity in the urine and kidney.

TABLE I

Biodistribution of $^{125}$I-Annexin V in a Rabbit with Arterial Thrombosis

| Tissue or fluid | | Counts per sec per gm specimen | Ratio specimen:blood |
|---|---|---|---|
| Blood | | 2080 | 1.00 |
| Clot[a]- | proximal portion | 35771 | 17.20 |
| artery | medial portion | 12980 | 6.24 |
| | distal portion | 5525 | 2.66 |
| Carotid[a]- | proximal portion | 9607 | 4.62 |
| artery | medial portion | 9833 | 4.73 |
| | distal portion | 4700 | 2.26 |
| Aorta | | 1527 | 0.73 |
| Vena cava | | 1620 | 0.78 |
| Kidney | | 60752 | 29.20 |
| Urine | | 32644 | 15.70 |
| Liver | | 1506 | 0.72 |
| Spleen | | 3141 | 1.51 |
| Heart | | 1905 | 0.92 |
| Lung | | 4893 | 2.35 |
| Skeletal muscle | | 1524 | 0.73 |

[a]The thrombosed carotid artery was removed and fixed in formalin. It was then sectioned in three pieces; for each piece, the thrombus was removed and the vessel and thrombus counted separately.

EXAMPLE V

Essentially identical results, as that presented in Example I, were obtained when thrombosis was induced in the femoral rather than the carotid artery.

EXAMPLE VI

Annexin/scuPA and annexin/plasminogen are activated by plasma kallikrein (or plasmin) and urokinase, respectively. Activated annexin/urokinase, annexin/plasmin and annexin/SK are incubated with plasminogen and the resulting plasmin is assayed using the synthetic substrate, Boc-Glu-Lys-Lys-MCA (Peptides International). The plasminogen activating activities of the hybrid molecules can be compared with that of the parent proteins.

The fibrinolytic activity of hybrids can be assayed by the method of RiJnen et al. (Thromb. Haemostas. (1984) 52, 308–310), except that platelet-rich plasma is used instead of platelet-poor plasma. Fresh human platelet-rich plasma is added to thrombin (or tissue factor), $CaCl_2$ and $^{125}$I-fibrinogen, immediately placed in silastic tubing (4 mm I.D.) and incubated at 37° C. for 30 minutes. The tubing is cut into pieces of defined length and clots are removed from the tube and washed with buffer. After the radioactivity is measured, the clots are incubated with the hybrids or the native proteins (for example, scuPA, SK or plasmin). Fibrinolytic activity is assessed by determining the solubilized radioactivity. The concentrations of fibrinogen and plasminogen in the sample plasma are assayed by ELISA to determine fibrinogenolysis.

EXAMPLE VII

Human single-chain urokinase-typeplasminogen activator (scuPA) was obtained from the Green Cross Co., Osaka, Japan. Sulfo-SMCC [sulfosuccinimidyl 4-(N-maleimidomethyl) cyclohexane-1-carboxylate] was purchased from Pierce, Rockford, Ill.

ScuPA was dialyzed overnight against 0.1M sodium phosphate, pH 7.3 containing 6M urea. After dialysis, the concentration of scuPA was adjusted to 32.5 µM.

Sulfo-SMCC was added to dialyzed scuPA aliquots at two final concentrations of 65 µM and 325 µM. The samples were incubated for 30 minutes at room temperature. At the end of incubation, glycine (10 mM) was added. The samples were applied to a gel filtration column (PD-10, Pharmacia) to remove excess unreacted reagents. The column then was eluted with 0.1M sodium phosphate buffer, pH 6.0 containing 6M urea and 10 mM EDTA. The protein fractions were pooled (scuPA-SMCC).

Annexin V was dialyzed overnight at room temperature against 0.1M sodium phosphate buffer, pH 7.3 containing 6M guanidine (or 8M urea). The sample was applied to a gel filtration column (PD-10) and eluted with 0.1M phosphate buffer, pH 6.0 containing 6M urea and 10 mM EDTA. The protein fractions were pooled (unfolded annexin V).

SMCC-scuPA was conjugated with unfolded annexin V by incubation overnight at room temperature. Aliquots of scuPA/annexin V conjugate were applied to SDS-polyacrylamide gels and were separated electrophoretically. SMCC-scuPA alone, annexin V alone and molecular weight markers served as controls. Formation of the conjugate was confirmed as a species of molecular weight equal to the sum of the molecular weights of the two components.

EXAMPLE VIII

ScuPA/annexin V conjugate as prepared in Example VII was activated by plasmin. Fifty microliters of scuPA/annexin V conjugate (approximately 500 IU/ml) were incubated with 50 µl of plasmin (0.9 µM) for 10 minutes at room temperature. Then 50 µl of aprotinin (10 µM) were added and the mixture was incubated for 5 minutes at room temperature to inhibit plasmin.

Next, 50 µl of the synthetic peptide substrate (2 mM), pyroGlu-Gly-Arg-p-nitroanilide (S-2444, Kabi, Sweden) were added and the mixture was incubated for 30 minutes at room temperature. The reaction was stopped by the addition of 1 ml of 10% acetic acid. The amount of p-nitroaniline produced was measured by absorbance at 405 nm. The activity was expressed as International Standard Units (IU).

ScuPA and scuPA to which one SMCC was bound showed equivalent activity. As the number of SMCC molecules bound to scuPA increased, the activity decreased slightly. At a ratio of 10 SMCC molecules to each scuPA molecule, the conjugate had a 25% reduction of activity.

EXAMPLE IX scuPA cDNA can be derived from any of a number of available scuPA clones, for example, plasmid psV-GI-preUK (JP-A-60-180591, EP-A-253241 or EP-A-15472). For Joining scuPA cDNA downstream of a promoter, such as at the ClaI site of the trp promoter (EP 0152830) and available in vectors pDR720 from PL Biochemicals and pGX112 from Genex, Gaithersburg, Md., a synthetic DNA having the following base sequence (SEQ ID NO: 2) can be used:

```
                                    M   S   N   E   L   H   Q   V   P   N
        XhoI       ClaI                                                  TthHB8I
5'-TCGAGCATCGATAAA ATG TCT AAC GAA TTG CAC CAA GTT CCA TCG-3'
                                    (SEQ ID NO:2)
```

The synthetic DNA comprises the nontranslated region from the ClaI site of scuPA to the ATG codon and the region ranging from the ATG codon to the TthHB8I site, which corresponds to the 10th amino acid residue, with an XhoI site upstream from the ClaI site for Joining to an expression vector capable of functioning in yeast as well. The synthetic DNA was ligated to the 5' terminus of scuPA cDNA to enable operably linking the scuPA cDNA to a trp promoter.

Annexin V cDNA can be derived from, for example, the clone of Funakoshi et al., (1987b) supra, FuJikawa et al., U.S. Pat. No. 4,937,324 or plasmid pPAP-I-1.6, see Example II. The synthetic DNA having the following base sequence was used as a hirudin linker (Biol. Chem. Hoppe-Seyler (1986) 367, 731–740) for joining the C-terminus of scuPA to the N-terminus of annexin V. The hirudin linker (synthesized using known techniques) comprises a base sequence encoding the 50th to 64th amino acid residues of the amino acid sequence of hirudin (SEQ ID NO: 3).

```
                                    UK <—||—> hirudin
Arg  Ile  Arg  Ser  His  Thr  Lys  Glu  Glu  Asn  Gly  Leu  Ala  Leu  Ser  His  Asn  Asp  Gly  Asp
AGG  ATC  CGC  AGT  CAC  ACC  AAG  GAA  GAG  AAT  GGC  CTG  GCC  CTC  TCT  CAC  AAC  GAC  GGC  GAC
BamHI hirudin <—||—> annexin V
Phe  Glu  Glu  Ile  Pro  Glu  Glu  Tyr  Leu  Ala  Gln  Val  Leu  Arg
TTC  GAA  GAA  ATC  CCG  GAA  GAA  TAC  CTG  GCA  CAG  GTT  CTC  AGA
Nsp(7524)V                                              DdeI
                            (SEQ ID NO:3)
```

A suitable strain of E. coli and a vector operable therein are selected. For example, plasmid pMT017 (FIG. 1) was constructed using plasmid pYNS, which was prepared by inserting a trp promoter/operator (p/o) into pBR322 (JP-A-60–160887 or EP-A-158230); and a second plasmid comprising a sequence prepared by ligating BglII linkers at both ends of trpA (trp attenuator which is a terminator having a poly tail, commercially available from PL Biochemicals) having the following base sequence:

5'-AAAAAAAAGCCCGCTCATTAGGCGGGCT-3'    (SEQ ID NO:4)

and inserting the resulting DNA fragment into the BamHI site of pUC9. The DNA fragments of interest were obtained and joined in accordance with conventional methods, for example, as described in Molecular Cloning, Cold Spring Harbor Laboratory (1982).

Plasmid pMT017 comprises under the control of the trp promoter, scuPA cDRA, a base sequence encoding 15 amino acid residues corresponding to the 50th to 64th amino acid residues of himdin, annexin V cDNA and the trp attenuator.

Plasmid pMT0 17 was introduced into an appropriate *E. coli* host, such as *E. coli* HB101 (Takara Shuzo, following the manufacturer's recommended procedures), and the resulting transformants were incubated overnight at 30° C. in L broth medium supplemented with 20 µg/ml ampicillin to obtain gene expression products. After the products were solubilized and reconstituted, the biological activity of the products was examined. The products were prourokinase/ annexin V conjugates (hybrid protein) having a molecular weight of about 85 k and reactive with both anti-urokinase antibody and anti-annexin V antibody (see, for example, Flaherty et al. supra). The products possessed thrombolytic activity as determined in a fibrin plate assay.

EXAMPLE X

Figure 2:
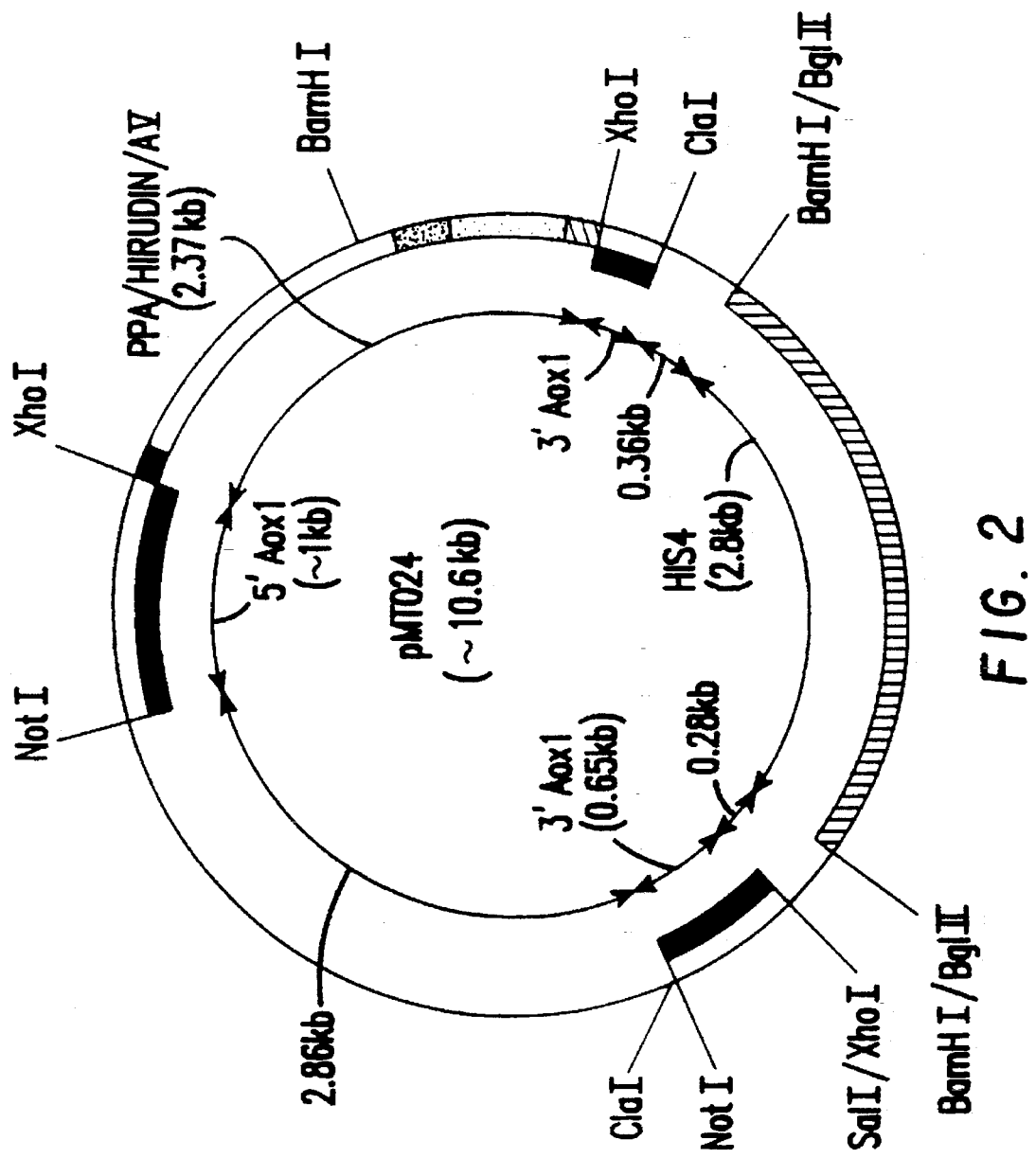
FIG. 2 depicts a map of recombinant plasmid pMT024. The Pichia AOX promoter region is denoted as 5'Axo1, the scuPA-hirudin-annexin V coding region is denoted as PPA/HIRUDIN/AV, the AOX terminator region is denoted as 3'Axo1 and the yeast selectable marker is denoted as HIS4. The solid black box just downstream from the XhoI site of the 5'Axo1 sequence represents the Mucor rennin signal sequence. The 2.86 kb sequence between the 3'Axo1 and 5'Axo1 sequences are pBR322-derived sequences. Sizes are noted in kilobases (kb) and commonly known and useful restriction sites are denoted.

Plasmid pMT024 (FIG. 2), a Pichia expression vector, was constructed using plasmids pMT017 and pAOS07NX, which was prepared by convening the EcoRI cloning site of plasmid pAO807N (JP-A-2–104290 or EP-A-344459) to an XhoI site using conventional methods described in, for example, Molecular Cloning, supra. Plasmid pMT024 comprises under the control of the AOX1 promoter, a base sequence corresponding to a signal sequence of Mucor rennin (Hiramatsu et al., J. Biol. Chem. (1989) 264, 16862) obtained from plasmid pJK1 (Gene (1991) 99, 235–241), scuPA cDNA, a base sequence encoding 15 amino acid residues of the 50th to 64th amino acid residues of hirudin and annexin V cDNA.

Plasmid pMT024 was introduced into an appropriate Pichia yeast host, such as *Pichia pastoris* GTS115 (NRRL Y-15851), following NotI digestion (The fragment was EtOH precipitated and suspended in TE buffer at a concentration of about 2 mg/ml. A 10µl portion was added to 100µl of competent cells. His+transformants were selected.) and the transformed cells were incubated at 30'C for 3 days in a medium containing 1% yeast extract, 2% Bacto Peptone and 1% MeOH to allow the cells to secrete gene expression products. The recombinant products were prourokinase/ annexin V conjugates (hybrid protein) having a molecular weight of about 85 k and reactive with both anti-urokinase antibody and anti-annexin V antibody. The products possessed thrombolytic activity in a fibrin plate assay.

EXAMPLE XI

Figure 3:
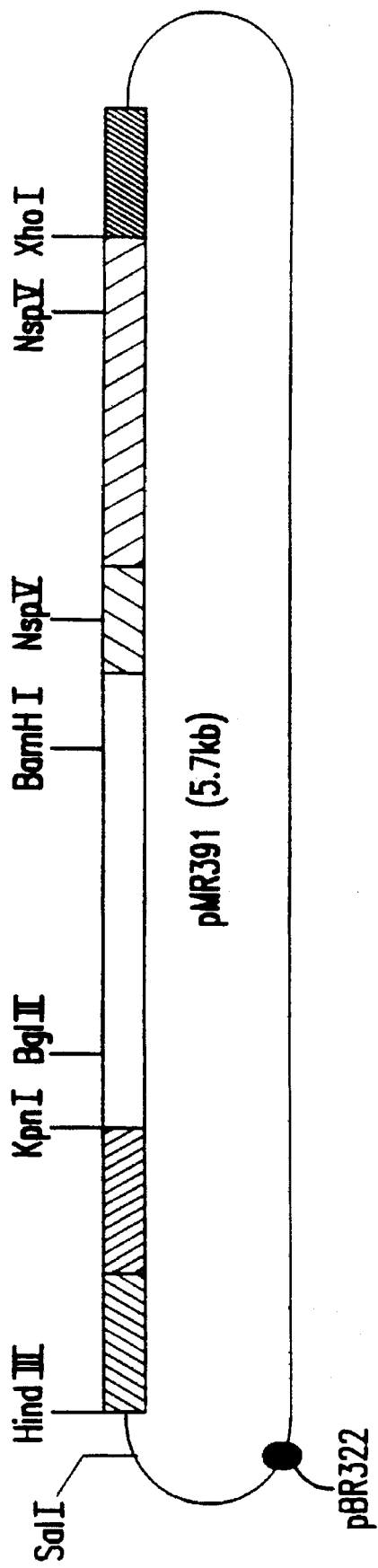
FIG. 3 depicts a map of recombinant plasmid pMR391. Beginning with the HindIII site, the first narrow right slanting cross hatched region is the SV40 enhancer and promoter, the second narrow left slanting cross hatched region is the SV40 splice junction, the third clear region is the PPA (scuPA) coding region, the fourth wide right slanting cross hatched region is the hirudin linker, the fifth wide left slanting cross hatched region is the annexin V coding region and the sixth region downstream from the XhoI site is the SV40 polyA region.

Plasmid pMR391 (FIG. 3), a CHO cell expression vector, was constructed using plasmids pMT017 and psV-G1-preUK, described hereinabove, in accordance with conventional methods, for example, described in Molecular Cloning, supra. Plasmid pMR391 comprises under the control of the SV40 enhancer/promoter, a SV40 splice junction, scuPA cDNA, a base sequence encoding 15 amino acid residues corresponding to the 50th to 64th amino acid residues of hirudin, annexin V cDNA and SV40 poly A signal sequences.

CHO cells were transformed with plasmid pMR391 and the transformed cells were cultivated at 37° C. for 3 days in MEM supplemented with 10% FCS to allow the cells to secrete gene expression products. The products were prourokinase/annexin V conjugates (hybrid protein) having a molecular weight of about 90 k and reactive with both anti-urokinase antibody and anti-annexin V antibody. The products possessed thrombolytic activity in a fibrin plate assay.

EXAMPLE XII

SMCC-scuPA, made using the techniques described hereinabove, is conjugated with modified annexin V with an additional cystsine residue at the N-terminus by incubation overnight at room temperature. (The modified annexin V was made by ligating to the 5' end of the annexin V coding sequence an oligonucleotide encoding about ten amino acids including a cysteine residue at the amino terminal end.) Aliquots of scuPA/modified annexin V conjugate are applied to SDS-polyacrylamide gels and are separated electrophoretically. SMCC-scuPA alone, modified annexin V alone and molecular weight markers serve as controls. Formation of the conjugate is confirmed as a species of molecular weight equal to the sum of the molecular weights of the two components.

EXAMPLE XIII

Annexin V (8 nmoles) in 250 µl of 50 mM triethanolamine (TEA)-HCl buffer, pH 8.0 containing 50 mM KCl and 1 mM $MgCl_2$, was mixed with 2.5 µl of β-mercaptoethanol (final concentration of 1%) and cooled to 0° C. Then varying concentrations of iminothiolane (10 µl ) were added to individual samples and allowed to stand for 20 min at 0° C. The samples were desalted on Fast Desalting columns (Pharmacia, HR10/10) with 50 mM Tris-HCl, pH 7.4 containing 50 mM NaCl, 1 mM EDTA and 0.05% $NaN_3$ (the buffer was flushed with $N_2$ before use) and protein-containing fractions (1.1 ml) were collected. The amount of newly introduced sulfhydryl group was determined using Ellman's reagent (Ellman, Arch. Biochem. Biophys. (1958) 74, 443). The clotting activity was determined as described above and the percent inhibitory activity was calculated from a standard curve constructed using authentic annexin V. The moles of sulfhydryl group (SH) per mole of annexin V and the percent clotting activity are shown in Table II. The inhibitory activity of annexin V was retained after modification.

TABLE II

| Sample | SH/annexin (mole/mole) | Concentration of 2-imino-thiolane used (µmole) | Clotting time (sec) | Activity (%) |
|---|---|---|---|---|
| 1 | 2.31 | 25.0 | 131 | 97 |
| 2 | 1.58 | 12.5 | 133 | 101 |
| 3 | 0.83 | 5.0 | 134 | 102 |
| 4 | 0.56 | 2.5 | 123 | 81 |
| 5 | 0.37 | 1.25 | 126 | 87 |
| 6 | 0.19 | 0.5 | 127 | 89 |
| 7 | 0 | 0 | 132 | 100 |

EXAMPLE XIV

ScUPA (20 nmol, 200 µl , specific activity of 417 U/mg) in 0.1M 2-(N-morpholino)ethanesulfonic acid (MES) buffer, pH 6.0 was mixed with varying concentrations of iodoacetic anhydride (IAA) in tetrahydrofuran at 0° C. IAA was added three times at 3 minute intervals. The sample then was applied over a Fast desalting column HR 10/10) using 50 mM Tris-HCl , pH 7.4 containing 50 mM NaCl , 1 mM EDTA and 0.05% NaN$_3$ (the buffer was flushed with N$_2$ before use).

The amount of iodoacetyl group (IA) introduced into scuPA was determined as follows: icdoacetyl-scuPA was mixed with known amounts of reduced glutathione and the remaining glutathione was assayed using Ellman's reagent. The amidolytic activity of iodoacetyl-scuPA was assayed using the peptide substrate, S-2444, after it was activated by plasmin. Table III shows the moles of iodoacetyl group per annexin V and the amidolytic activity of iodoacetyl-scuPA. The results indicate that iodoacetyl-scuPA has the same amidolytic activity as intact scuPA.

TABLE III

| Sample | Mole IA/ mole/scuPA | IAA used (μmole) | Amidolytic activity (O.D.$_{405}$) | Activity (%) |
| --- | --- | --- | --- | --- |
| 1 | 0.72 | 2.4 | 0.165 | 98 |
| 2 | 0.44 | 1.6 | 0.163 | 94 |
| 3 | 0.54 | 0.8 | 0.169 | 106 |
| 4 | 0 | 0 | 0.174 | 100 |

EXAMPLE XV

Sulfhydryl-annexin V and iodoacetyl-scuPA that were prepared as described above were mixed and allowed to stand for 1 hour at 37° C. in dark. The products were applied to and separated in an SDS-polyacrylamide gel and examined by immunoblot analysis using anti-scuPA and anti-annexin V antibodies (6.7 nmol of three different preparations of sulfhydryl-annexin V, i.e., moles of sulfhydryl group/annexin, 1.31, 0.82 and 0.57, were conjugated with 6.7 nmol of iodoacetyl-scuPA).

Bands that migrated as a species of molecular weight of about 92,000 were detected by both antibodies showing that the 92,000 species is a conjugate (hybrid protein) of annexin V/scuPA. More conjugates were formed if annexin V has a higher sulfhydryl group content and no conjugate was formed when unmodified annexin V was used.

EXAMPLE XVII

Annexin V-N1 is designed to be an amino-terminally extended molecule in which the sequence of Met-Ala-Cys-Pro-Ser-Gly-Gly-Pro-Ser-Gly-Gly-Pro-Met (SEQ ID NO: 5) is connected to the amino-terminal Ala residue of mature annexin V. The SH group of the third Cys residue may be used for conjugates with iodoacetyl-scuPA.

For the construction of annexin V-N1 DNA, two complementary oligonucleotides containing NcoI sites, (5'-CATGGCATGCCCGTCTGGTGGTCCGTCTGGTGG TCC-3'(SEQ ID NO: 6) and 5'-CATGGGACCACCAGACCGACCACCAGACGGGCA TGC-3'(SEQ ID NO: 7) were synthesized, purified, phosphorylated and annealed by standard methods. The plasmid pPAP-1-319 (Tait & Smith, Arch. Biochem. Biophys. (1991) 288, 141) was digested with NcoI. The double-stranded oligonucleotide then was ligated into the plasmid to create plasmid, pPAP-I-N1. DNA sequencing confirmed that the recombinant plasmid contained the intended sequence. The recombinant protein was expressed and purified as described (Tait & Smith, supra.

Transformed E. coli cells were collected from 10 liters of culture medium and washed once with 50 mM Tris-HCl buffer, pH 7.4 containing 50 mM NaCl. Cells were suspended in 250 ml of phosphate buffer, pH 7.4 containing 6M urea, 1% Triton X-100, 0.1mM diisopropyl fluorophosphate and 10 mM EDTA and sonicated for 3×1 min. The cell lysate was centrifuged for 20 min at 15,000 rpm and the supernatant was collected followed by dialysis against 50 mM Tris-HCl buffer, pH 7.4 containing 50 mM NaCl, 1 mM EDTA. The sample then was applied to a Mono Q column (Pharmacia) with the same buffer and eluted with an NaCl gradient (0.05–1M). Annexin V-N1 was detected by dot-blot and the fractions containing annexin V-N1 were pooled and concentrated by ultrafiltration. The concentrated sample was applied to a TSKgel G3000 SWXL (20×500 mm) column and the fractions containing annexin V-N1 (detected by dot-blot) were pooled and concentrated. The inhibitory activity of annexin V-N1 was determined by clotting activity as described above and the results shown that annexin V-N1 and the activity as described above and the results showed that annexin V-N1 and the wild type annexin have similar activities. The protein sequence analysis confirmed that annexin V-N1 had the intended amino terminal oligopeptide with deletion of the amino terminal methionine.

All references cited herein are herein incorporated by reference in entirety.

It will be appreciated that the methods and compositions of the present invention are capable of being incorporated in the form of a variety of embodiments, only a few of which have been illustrated and described above. The invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within the scope of the invention.

We claim:

1. A conjugate comprising:
   (a) an annexin covalently linked to
   (b) urokinase.

2. A therapeutic composition comprising in an amount effective to lyse thrombi, a conjugate of
   (a) an annexin covalently linked to
   (b) urokinase;
   (c) and a said composition contains a pharmaceutically acceptable carrier, diluent or excipient.

3. A method of lysing thrombi comprising administering to a host in need of treatment a therapeutically effective amount of a composition comprising:
   (1) a conjugate comprising:
      (a) an annexin covalently linked to
      (b) urokinase; and
   (2) a pharmaceutically acceptable carrier, diluent or excipient.

* * * * *